United States Patent [19]
Strittmatter et al.

[11] Patent Number: 5,994,527
[45] Date of Patent: *Nov. 30, 1999

[54] FUNGUS-RESPONSIVE CHIMERIC GENE

[75] Inventors: Gunter Strittmatter; Norbert Martini, both of Köln, Germany

[73] Assignee: Max-Planck-Gesellschaft zur Forderung der Wissenschaften E.V., Munich, Germany

[*] Notice: This patent is subject to a terminal disclaimer.

[21] Appl. No.: 08/911,145

[22] Filed: Aug. 14, 1997

Related U.S. Application Data

[62] Division of application No. 08/302,891, filed as application No. PCT/EP93/00700, Mar. 22, 1993, Pat. No. 5,859,332.

[30] Foreign Application Priority Data

Mar. 20, 1992 [EP] European Pat. Off. .............. 92400770

[51] Int. Cl.$^6$ ............................ C12N 15/29; C12N 15/82
[52] U.S. Cl. ........................ 536/24.1; 536/23.6; 800/279; 800/287; 800/301; 435/6
[58] Field of Search ................................. 536/23.6, 24.1; 800/279, 287, 301; 435/6

[56] References Cited

U.S. PATENT DOCUMENTS 5,723,760  3/1998  Strittmatter ............................. 800/205

FOREIGN PATENT DOCUMENTS

| | | |
|---|---|---|
| 0 375 091 | 6/1990 | European Pat. Off. . |
| 0 412 911 | 2/1991 | European Pat. Off. . |
| 91/15585 | 10/1991 | WIPO . |
| 92/04453 | 3/1992 | WIPO . |
| 92/21751 | 12/1992 | WIPO . |

OTHER PUBLICATIONS

*Molecular Plant–Microbe Interactions*, "Structural Analysis and Activation by Fungal Infection of a Gene Encoding a Pathogenesis–Related Protein in Potato", Janet L. Taylor, et al., vol. 3, No. 2, pp. 72–77, 1990.

*Plant Science*, "Transformation of Japanese Potato Cultivars with the β–Glucuronidase Gene Fused with the Promoter of the Pathogenesis–Related 1a Protein Gene of Tobacco", Teruo Ishige, et al., vol. 73 (1991), pp. 167–174.

*Chemical Abstracts*, vol. 111, No. 23, Dec. 4, 1989, Abstract No. 212143j, Urs Christ, et al.

*Biosis Previews Database*, Abstract No. 87130376, J. Joosten, et al.

Oshima et al., "Analysis of Stress–Induced or Salicyclic Acid–Induced Expression of the Pathogenesis–Related 1a Protein Gene in Transgenic Tobacco", *The Plant Cell*, vol. 2, 95–106, Feb. 1990.

Ohashi et al. 1990, Japanese Agricultural Research Quarterly 24(2):91–99.

Mariani et al. 1990 *Nature*, 347:737–741.

Sambrook et al. p. 7.52 In: Molecules Cloning—A Laboratory Manual, Second Edition, Cold Spring Harbor Press: Plainview, NY, 1989.

*Primary Examiner*—David T. Fox
*Attorney, Agent, or Firm*—Burns, Doane Swecker & Mathis, LLP

[57] ABSTRACT

A method for isolating a fungus-responsive promoter comprising the steps of:

(i) identifying a promoter sequence in the genomic DNA of a plant using a promoter-effective portion of the promoter of the gene of SEQ ID No. 1 as a hybridization probe, and (ii) isolating said fungus-responsive promoter.

12 Claims, 4 Drawing Sheets

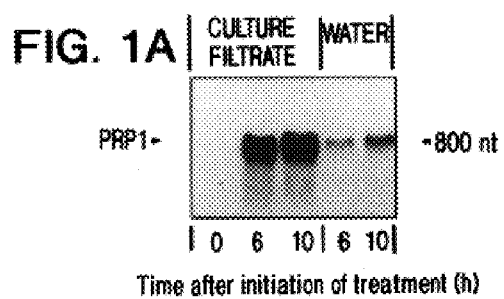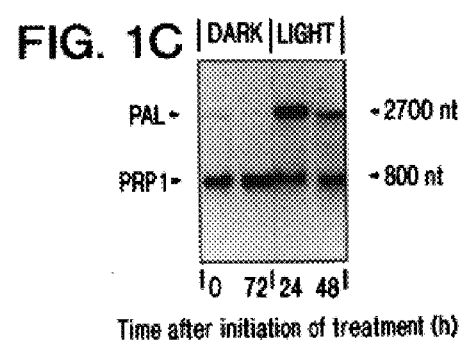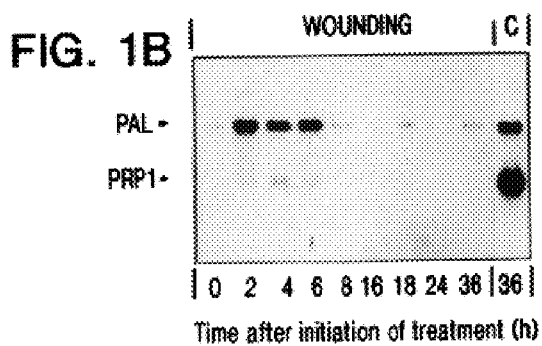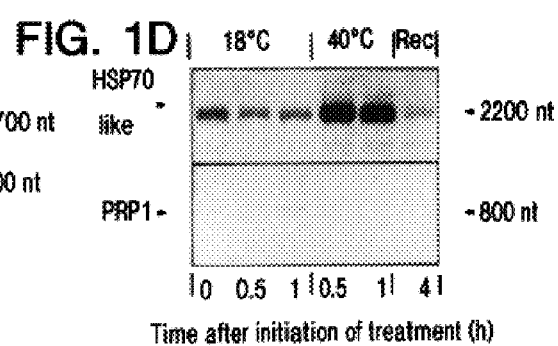

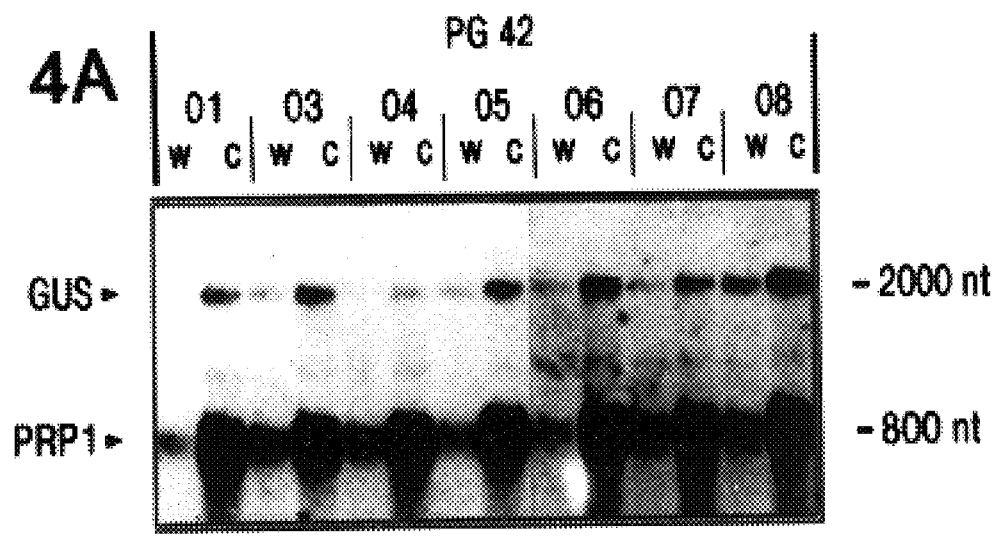
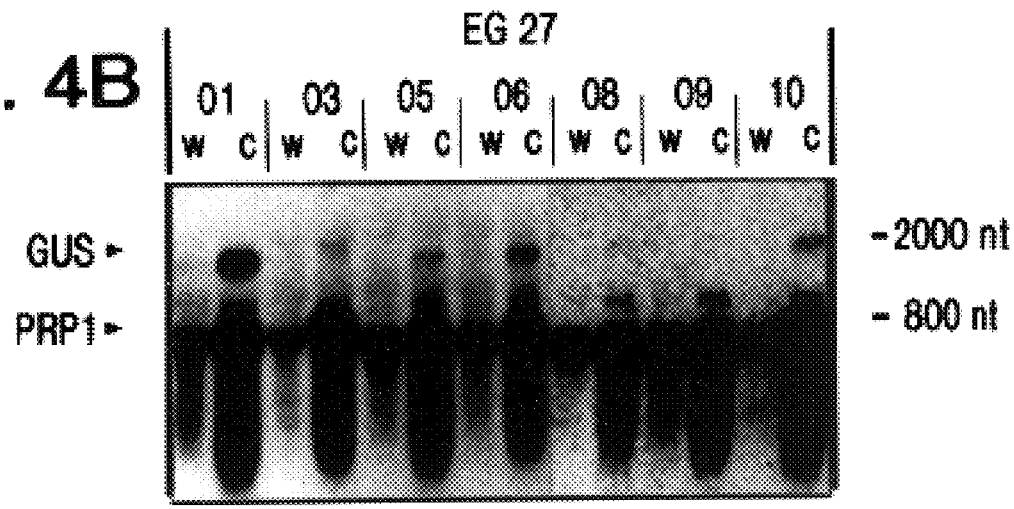
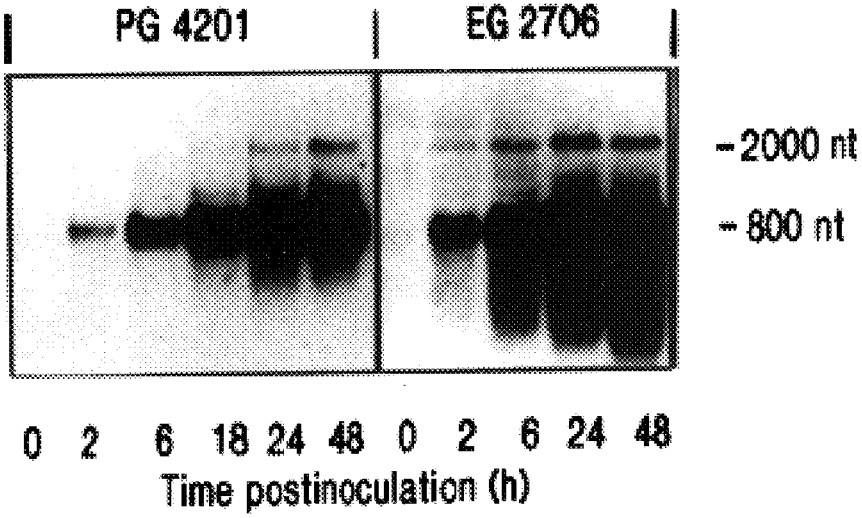

5,994,527

FUNGUS-RESPONSIVE CHIMERIC GENE

This application is a divisional of application Ser. No. 08/302,891, filed Jan. 30, 1995, now U.S. Pat. No. 5,859,332, which is a 371 of PCT/EP93/00700 filed Mar. 22, 1993.

BACKGROUND OF THE INVENTION (i) Field of the Invention

This invention relates to the use, in a transgenic plant, of at least a portion of a fungus-responsive promoter to induce (i.e., stimulate), in response to a fungus infection of the plant, the expression of a gene or a DNA fragment substantially selectively in cells of the plant around the site of the fungal infection. The use of the fungus-responsive promoter of this invention is especially valuable in transgenic plants for controlling a foreign gene or a DNA fragment that is to be expressed selectively in the cells of the plant which immediately surround the fungal infection site so as to render the plant resistant to the infecting fungus, particularly a plant-pathogenic fungus.

This invention also relates to a first or fungus-responsive chimaeric gene that can be used to transform a plant and that contains a first foreign DNA that:
  a) encodes a product which, when expressed in cells of the plant immediately surrounding a fungal infection site, can either i) kill or at least adversely disturb significantly the plant cells immediately surrounding the fungal infection site or ii) kill, disable or repel one or more fungi in the fungal infection site; and
  b) is under the control of at least a portion of the fungus-responsive promoter of this invention.

This invention further relates to a cell of a plant, the genome of which is transformed to contain the first chimaeric gene and optionally a second or restorer chimaeric gene; the second chimaeric gene contains a second promoter that controls a second foreign DNA encoding a product which can inhibit or inactivate the first foreign DNA or its encoded product at least in cells of the plant other than those immediately surrounding a fungal infection site, particularly when the first foreign DNA encodes a product that can kill or adversely disturb significantly such other plant cells.

This invention yet further relates to: a) the fungus-resistant transgenic plant, such as a Solanaceae (e.g., tomato or potato) or Brassicaceae (e.g., oilseed rape), which is regenerated from the plant cell of this invention transformed with the first and optionally the second chimaeric genes of this invention, b) fungus-resistant transgenic plants derived from the regenerated transgenic plant and seeds of such plants, and c) plant cell cultures, all of which consist essentially of the transformed plant cells of this invention.

The plants of this invention are characterized by the fungus-responsive expression of the first chimaeric gene of this invention in plant cells surrounding, preferably immediately surrounding, the fungal infection site and either:
  a) the substantial, preferably complete, absence of expression of the first chimaeric gene in all other plant cells; or
  b) the substantial absence and preferably the complete absence, by expression of the second chimaeric gene of this invention, of the effects of any expression of the first chimaeric gene in all other plant cells—thereby rendering the plants resistant to fungal infections.

(ii) Description of Related Art

The fungi are a very old group of microorganisms. Harmful fungi cause diseases of man, other animals, and especially plants. About 8000 species of fungi can cause plant diseases, and all plants are attacked by some kind of fungi. Some plant-pathogenic fungi can attack many plant species, others attack only one.

In general, fungal plant diseases can be classified into two types: those caused by soilborne fungi and those caused by airborne fungi. Soilborne fungi cause some of the most widespread and serious plant diseases, such as root and stem rot caused by Fusarium spp. and root rot caused by Phytophthora spp.

Since airborne fungi can be spread long distances by wind, they can cause devastating losses, particularly in crops which are grown over large regions. A number of these pathogens have caused widespread epidemics in a variety of crops. Important diseases caused by airborne fungi are stem rust (*Puccinia graminis*) on wheat, corn smut (*Ustilago maydis*) on corn, and late blight disease (*Phytophthora infestans*) on potato and tomato.

Most of these fungal diseases are difficult to combat, and farmers and growers must use a combination of practices, such as sanitary measures, resistant cultivars, and effective fungicides, against such diseases. Hundreds of million of dollars are spent annually for chemical control of plant-pathogenic fungi. As a result, there is today a real need for new, more effective and safe means to control plant-pathogenic fungi.

It is known that plants possess defense mechanisms against fungal diseases. When a plant recognizes a fungal attack, it can respond by inducing several reactions in its cells immediately surrounding the fungal infection site. Resistance mechanisms are activated by the initial infection, so as to limit the spread of the invading fungal pathogen (Ward et al, 1991). The resistance mechanisms include a localized cell death known as a hypersensitive response, the accumulation of phytoalexins, and lignification (De Wit, 1987). The specificity of these responses, which can be very effective in limiting the spread of a fungal infection, depends on the genetic make-up of the host and the pathogen.

Characterization of the genetic components which control cultivar/race specific host/pathogen interactions is a goal of current molecular plant pathology research. Transcriptional activation of defense-related genes is part of the complex defense system which enables plants to deal with contacts with potential pathogens (Collinge and Slusarenko, 1987; Hahlbrock and Scheel, 1989; Bowles, 1990). The identification of cis-acting elements regulating the expression of defense-related genes has been sought in order to elucidate the process by which signal transduction chains connect the initial recognition of a pathogen by a plant host with its induction of defense reactions (Lamb et al, 1989). As found for several other host/pathogen systems (van Loon, 1985; Hahlbrock and Scheel, 1989), infection of potato with the fungus *Phytophthora infestans,* which is the causal agent of late blight disease, leads to transcriptional activation of genes encoding enzymes of the phenylpropanoid metabolism and PR-proteins (Fritzemeier et al, 1987; Kombrink et al, 1988; Taylor et al, 1990). Transcription of these genes is induced with similar kinetics in compatible and incompatible interactions of different potato cultivars with different *Phytophthora infestans* races. The nucleotide and deduced amino acid sequences of one of the "pathogenesis related" (or "PR")-protein genes in potato, i.e., prp1-1, which is a member of the large prp1 gene family (with 10–15 very similar copies per haploid genome), shows striking similarity to the corresponding sequences of a gene encoding the HSP26 heat-shock protein in soybean (Taylor et al, 1990). In situ hybridization experiments showed that the PRP1 transcript accumulates around the site of fungal penetration, but the function of this protein in the defense strategy of potato is not yet clear. The homologous soybean HSP26 protein represents a unique member within a group of low molecular weight heat-shocked proteins of plants, missing some characteristic structural features and appearing in an unusually high relative concentration under a broad variety of stress conditions (Czarnecka et al, 1984; Vierling, 1991) but also having no known role in cell metabolism. No sequence similarity has been found between the protein encoded by the prp-1-1 gene and several know PR-proteins from other Solanaceous species (Taylor et al, 1990).

Most plant genes encoding proteins related to pathogen defense, analyzed to date on the level of cis-acting elements, are also activated by several other stress stimuli like mechanical wounding, light and/or elevated concentrations of heavy metals (Oshima et al, 1990; Schmid et al, 1990; Stermer et al, 1990; Douglas et al, 1991; Joos and Hahlbrock, 1992; Becker-Andre et al, 1991).

SUMMARY OF THE INVENTION

In accordance with this invention is provided the first or fungus-responsive chimaeric gene that comprises the following, operably linked, DNA sequences:

1) the fungus-responsive promoter, which preferably comprises all or promoter-effective portions of a prp1 promoter, especially all or promoter-effective portions of the prp1-1 promoter, particularly promoter-effective portions of the prp1-1 promoter fragment between nucleotides 1 and 696 of SEQ ID no. 1 described in the Sequence Listing, more particularly the promoter fragment between nucleotides 295 and 567 of SEQ ID no. 1 described in the Sequence Listing, and which can direct transcription of a foreign DNA substantially selectively, preferably selectively, in cells of a plant surrounding, preferably immediately surrounding, a site of an infection of the plant by a fungus, particularly a plant-pathogenic fungus such as a Phytophthora (e.g., *P. infestans*) or a Cladosporium (e.g., *Cladosporium fulvum*);

2) the first foreign DNA that encodes a first RNA and/or protein or polypeptide which, when produced or overproduced in cells of the plant which surround, preferably immediately surround, the fungal infection site, either a) kills, disables or repels the fungus or b) kills or at least disturbs significantly the metabolism, functioning and/or development of the plant cells surrounding, preferably immediately surrounding, the fungal infection site, so as to limit further spread of the fungus; and 3) suitable 3' transcription termination signals (i.e., 3' end) for expressing the first foreign DNA substantially selectively, preferably selectively, in cells of the plant which surround, preferably immediately surround, the fungal infection site.

Also in accordance with this invention is provided a cell of the plant, in which the nuclear genome is transformed to contain the first chimaeric gene of this invention and optionally—especially when the fungus-responsive promoter directs transcription of the first foreign DNA only substantially selectively in plant cells immediately surrounding the fungal infection site, particularly when the first foreign DNA is of type b) above—to contain also the second or restorer chimaeric gene, preferably in the same genetic locus; the second chimaeric gene comprises the following, operably linked, DNA sequences:

1) the second promoter, such as a relatively weak constitutive promoter (e.g., the nos promoter), which can direct transcription of a foreign DNA in at least cells of the plant other than those surrounding, preferably other than those immediately surrounding, the fungal infection site;

2) the second foreign DNA that encodes a second RNA and/or protein or polypeptide which, when produced or overproduced in at least such other cells of the plant, can inhibit or inactivate the first foreign DNA or the first RNA or protein or polypeptide in at least such other cells of the plant; and 3) suitable 3' transcription termination signals for expressing the second foreign DNA in at least such other cells of the plant.

Further in accordance with this invention are provided: the fungus-resistant plant regenerated from the transformed plant cell of this invention, fungus-resistant plants derived therefrom and their seeds, and plant cell cultures, each of which consists essentially of the transformed plant cells of this invention.

Still further in accordance with this invention is provided a process for rendering a plant resistant to one or more fungi, particularly plant-pathogenic fungi such as Phytophthora (e.g., *P. infestans*) and Cladosporium (e.g., *Cladosporium fulvum*), comprising the step of transforming the plant's nuclear genome with the first chimaeric gene and optionally the second chimaeric gene of this invention.

BRIEF DESCRIPTION OF THE DRAWINGS

FIGS. 1A–1D depict an accumulation pattern of PRP1 mRNA response to different abiotic stimuli in Example 1;

FIGS. 4A–4C depict transcript accumulation in individual transformants after infection with *P. infestans* in Example 2.

DETAILED DESCRIPTION OF THE INVENTION

Figure 2A:
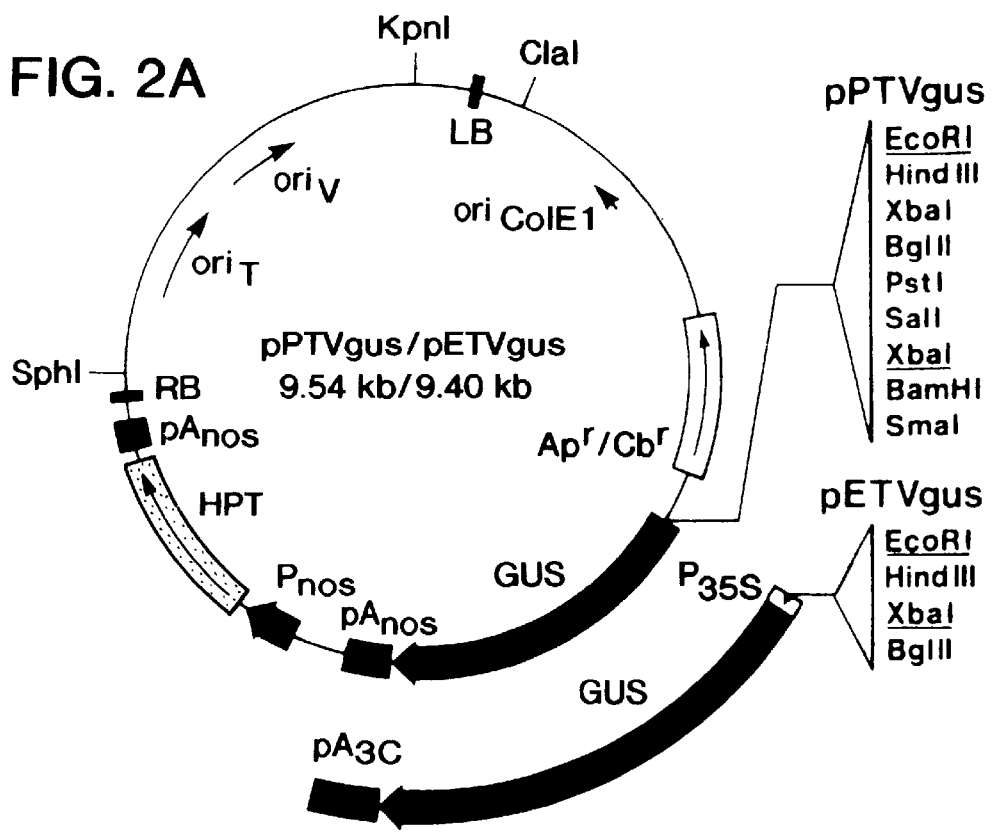
FIGS. 2A–2B are a schematic drawing of vectors and their DNA inserts used in Example 2.

Throughout this Description, the following definitions apply:

"Fungus-infected plant" means a plant which is infected by at least one fungus species, particularly plant-pathogenic fungus species, such as Phytophthora spp, Pythium spp. Fusarium spp, Sclerotinia spp, Puccinia spp, Ustilago spp, Alternaria spp, Helminthosporium spp., *Pyrenoperiza brassicae, Cylindrosporium concentricum, Phoma lingam* and *Leptosphaeria maculans,* as well as *Botrytis cinerea, Erysiphe cruciferorum, Peronospora parasitica, Plasmodiophora brassicae, Pseudocercosporella capsella,* Septoria spp, Pyrenophora spp, Ustilago spp, Botrytis spp, and Erysiphe spp.

"Fungus-responsive promoter" means a promoter, whose action in controlling transcription of a DNA sequence (e.g., gene) in a plant is: 1)influenced—that is, induced (i.e., stimulated)—by infection of the plant by a fungus, particularly a plant-pathogenic fungus; and 2) occurs substantially selectively, preferably exclusively, in plant cells around the fungal infection site, preferably in plant cells immediately surrounding the fungal infection site. The term "fungus-responsive promoter" also encompasses portions of a fungus-responsive promoter (hereinafter "promoter-effective portions") which are at least as effective, and are preferably significantly more effective, in directing transcription of a first foreign DNA of this invention substantially selectively, preferably exclusively, in cells of a plant surrounding, preferably immediately surrounding, a fungal infection site. A preferred fungus-responsive promoter of this invention is the promoter of a prp1 gene, especially the prp1-1 gene, particularly promoter-effective portions of the fragment of the prp1-1 promoter in SEQ ID no. 1 between nucleotides 1 and 696. Preferred promoter-effective portions of the prp1-1 promoter between nucleotides 1 and 696 of SEQ ID no. 1 are those portions which are between nucleotides 295 and 696 of SEQ ID no. 1, such as those portions which are between nucleotides 295 and 567 of SEQ ID no. 1. It is believed that such promoter-effective portions of the prp1-1 promoter can provide better selectivity of expression in plant cells immediately surrounding a fungal infection site and/or enhanced levels of expression of the first foreign DNA in plant cells immediately surrounding a fungal infection site in response to a fungal infection. Indeed, the prp1-1 promoter fragment between nucleotide positions 295 and 567 of SEQ ID no. 1 has been found to provide better selectivity and enhanced levels of expression.

"Artificial hypersensitive cell death" refers to a plant defense mechanism which is conferred by a first chimaeric gene of this invention on a plant transformed therewith and which involves necrosis of plant cells at a fungus pathogen infection site, thereby limiting further spread of the fungus. This mechanism is analogous to a natural hypersensitive cell death occurring in incompatible plant/pathogen interactions.

"Homologous" refers to proteins or nucleic acids which have similar, preferably essentially the same, sequences of amino acids or nucleotides, respectively, and thus have substantially the same, preferably essentially the same, structural and/or functional properties.

"Foreign" with regard to a DNA sequence, such as a first or second foreign DNA of this invention, means that such a DNA is not in the same genomic environment (e.g., not operably linked to the same promoter and/or 3' end) in a plant cell, transformed with such a DNA in accordance with this invention, as is such a DNA when it is naturally found in a cell of the plant, bacteria, animal, fungus, virus or the like, from which such a DNA originates.

In accordance with this invention, a fungus-resistant plant can be produced from a single cell of a plant by transforming the plant cell in a known manner to stably insert, into its nuclear genome, the first chimaeric gene of this invention which comprises at least one first foreign DNA that is: under the control of, and fused at its upstream (i.e., 5') end to, a fungus-responsive promoter of this invention; and fused at its downstream (i.e., 3') end to suitable transcription termination (or regulation) signals, including a polyadenylation signal. Preferably, in the first chimaeric gene, only promoter-effective portions of the fungus-responsive promoter are used, in combination with a TATA box and other conventional promoter elements, such as an enhancer, of the fungus-responsive promoter or of another promoter, such as one of the constitutive plant-expressible promoter that can be used as the second promoter (e.g., a 35S promoter). Thereby, the first RNA and/or protein or polypeptide is produced or overproduced at least predominantly, preferably substantially exclusively, expecially exclusively, in those plant cells around, preferably immediately surrounding, a fungal infection site.

Optionally, the plant cell genome can also be stably transformed with the second chimaeric gene comprising at least one second foreign DNA that is: under the control of, and is fused at its 5' end to, the second promoter which is capable of directing expression of the second foreign DNA at least in cells of the plant where the first foreign DNA is expressed in other than those surrounding the fungal infection site and preferably substantially selectively in plant cells where the first foreign DNA is expressed in other than those immediately surrounding the fungal infection site; and fused at its 3' end to suitable transcription termination signals, including a polyadenylation signal. The second chimaeric gene is preferably in the same genetic locus as the first chimaeric gene, so as to guarantee with a high degree of certainty the joint segregation of both the first and second chimaeric genes into offspring of the plant regenerated from the transformed plant cell. However in some cases, such joint segregation is not always desirable, and the second chimaeric gene could be in a different genetic locus from the first chimaeric gene.

In accordance with this invention, the first foreign DNA in the first chimaeric gene is a gene or DNA fragment that encodes a first RNA and/or protein or polypeptide which, when produced or overproduced in the plant cells surrounding, preferably immediately surrounding, a site of a fungus infection, either: a) kills such surrounding plant cells or at least disturbs significantly their metabolism, functioning and/or development so as to induce an artificial hypersensitive cell death in order to limit the further spread of the invading fungus; and/or b) kills, disables or repels the fungus when it further infects such surrounding plant cells. First foreign DNAs preferably encode, for example, the following which can kill the surrounding plant cells or at least disturb significantly their metabolism, functioning and/or development: RNases such as RNase T1 or barnase; DNases such as endonucleases (e.g., EcoRI); proteases such as a papain; enzymes which catalyze the synthesis of photohormones, such as isopentenyl transferase or the gene products of gene 1 and gene 2 of the T-DNA of Agrobacterium; glucanases; lypases; lipid peroxidases; plant cell wall inhibitors; or toxins such as the A-fragment of diphtheria toxin or botulin. Other preferred examples of such first foreign DNAs are antisense DNAs encoding RNAs complementary to genes encoding products essential for the metabolism, functioning and/or development of the surrounding plant cells. First foreign DNAs also preferably encode, for example, the following first polypeptides or proteins which can kill, repel or disable fungi: lytic enzymes, such as chitinases and β-1,3 glucanases, that catalyze the hydrolysis of fungal cell walls; protease inhibitors (Ryan, 1990); and lectins (Broekaert et al, 1989); as well as other plant proteins with antifungal activity, such as the small basic peptide, CMIII, isolated from corn (European patent publication ("EP") 465 009) and the osmotin-like proteins (EP 460 753), as well as the antifungal peptides from *Amaranthus caudatus* seeds described by Broekaert et al. (1992) Biochemistry 31, 4308–4314, the antifungal peptides from *Mirabilis jalapa* seeds described by Cammue et al (1992) J. Biol. Chem. 267, 228–2233, the antifungal peptides from *Aspergillus giganteus* described in PCT publication WO 91/19738 (Schell et al), the basic peptide CMIII from maize seed described in EP 465 009, the Rs-AFP proteins obtained from radish described by Terras et al (1992) J. Biol. Chem. 267, 15301–15309, and genes encoding phytoalexins (Hain et al., Nature 361, 153). The first foreign DNA can also be an avirulence gene (e.g., the avr9 gene) and/or the corresponding resistance gene (e.g. the Cf9 gene) as described in PCT patent publication WO 91/15585.

Plants transformed with such a first foreign DNA in a first chimaeric gene of this invention will be resistant to fungal infections either: because of the plants' fungus-responsive breakdown, in a substantially selective manner, of their plant cells which surround, preferably immediately surround, the fungal infection site, thereby providing a hypersensitive response; or because fungi will be killed, repelled or disabled by, for example, a fungal toxin produced in situ substantially selectively by the plant cells surrounding, preferably immediately surrounding, the fungal infection site.

A fungus-responsive promoter of this invention and its promoter-effective portions, which can be used to control expression of the first foreign DNA of this invention substantially exclusively, preferably exclusively, in plant cells which surround, preferably immediately surround, a fungal infection site, can be identified and isolated in a well known manner in cells of fungus-infected plants. For example, a suitable fungus-responsive promoter can be identified and isolated in one or more plants, preferably two or more plants (e.g., oilseed rape, corn, and potato), infected by a fungus, by the following process steps for each plant:

1. searching for an mRNA, which is present at an elevated level in tissues (e.g. leaves) of the plant only after fungus infection thereof, by constructing a cDNA library of the fungus-infected plant and subjecting the cDNA library to differential screening;
2. isolating the cDNA that corresponds to the fungus-responsive mRNA (The fungus-responsive cDNA can also be isolated by the method of Hodge et al [1990]);
3. using this cDNA as a probe to identify the regions in the plant genome which contain DNA coding for the fungus-responsive mRNA; and then
4. identifying the portion of the plant genome that is upstream (i.e., 5') from this DNA and that codes for the fungus-responsive promoter of this DNA.

A preferred fungus-responsive promoter, obtained by this process from potato, is the promoter of a prp1 gene, especially the prp1-1 gene, particularly prompter-effective portions thereof which are between nucleotides 1 and 696 of SEQ ID no. 1, quite particularly promoter-effective portions thereof between nucleotides 295 and 696 of SEQ ID no. 1, more quite particularly promoter-effective portions thereof between nucleotides 295 and 567 of SEQ ID no. 1. Surprisingly, the fungus-responsive prp1-1 promoter is not inducible by heat-shock, wounding, light (e.g., ultraviolet light) or incubation with a heavy metal salt (however, the native full length prp1-1 promoter is inducible by CdCl). It is believed that other fungus-responsive promoters of this invention, homologous, for example, to the prp1-1 promoter and its promoter-effective portions, can be identified in the genomic DNA of other plants (e.g., rapeseed, corn, etc.) using the promoter fragment between nucleotides 1 and 696 of SEQ ID no. 1 or preferably promoter-effective portions thereof as hybridization probes in a conventional manner.

By "contventional methods" is meant that the filters are prehybridized for 1 to 2 hours in either 50% formamide, 5x SSPE, 2x Denhardt's reagent and 0.1% SDS at 42° C. or 6x SSC, 2x Denhardt's reagent and 0.1% SDS at 68° C. The denatured radiolabeled probe is then added directly to the prehybridization fluid and incubation is carried out for 16 to 24 hours at the appropriate temperature. After incubation, the filters are then washed for 20 minutes at room temperature in 1x SSC, 0.1% SDS, followed by three washes of 20 minutes each at 68° C. in 0.2x SSC and 0.1% SSC and 0.1% SDS. An autoradiograph is established by exposing the filters for 24 to 48 hours to X-ray film (Kodak XAR-2 or equivalent) at −70° C. with an intensifying screen.

When the fungus-responsive promoter in the first chimaeric gene of this invention is not 100% specific for the cells of the plant immediately surrounding the fungal infection site, and particularly when the first foreign DNA encodes a first RNA, polypeptide or protein killing the plant cells or adversely disturbing significantly the plant cells' metabolism, functioning and/or development, it is preferred that the plant cell genome be further transformed so that its nuclear genome contains, stably integrated therein, the second or restorer chimaeric gene of this invention. The second promoter of the second chimaeric gene is selected so that it is capable of directing transcription of the second foreign DNA to provide sufficiently high expression levels of the second RNA, protein or polypeptide to inhibit or preferably inactivate the first foreign DNA or any first RNA, protein or polypeptide expressed in at least substantially all plant cells other than those which surround, preferably in at least substantially all plant cells other than those which immediately surround, the fungal infection site. Examples of suitable plant-expressible second promoters are: the strong constitutive 35S promoters of the cauliflower mosaic virus of isolates CM 1841 (Gardner et al, 1981), CabbB-S (Franck et al, 1980) and CabbB-JI (Hull and Howell, 1987); the relatively weaker constitutive nos promoter (De Picker et al, 1982); and wound-inducible promoters, such as the TR1' and TR2' promoters which drive the expression of the 1' and 2' genes, respectively, of the T-DNA (Velten et al, 1984). Alternatively, a second promoter can be utilized which is specific for one or more plant tissues or organs (such as leaves), particularly specific tissues or organs (such as root tips) not infected by a fungus where the first foreign DNA is nevertheless expressed, whereby the second chimaeric gene is expressed only in such specific plant tissues or organs. Another alternative is to use a promoter whose expression is inducible (e.g., by temperature or chemical factors).

In accordance with this invention, the second foreign DNA in the second chimaeric gene is a gene or DNA fragment that encodes a second RNA and/or protein or polypeptide which, when produced or overproduced in cells of a plant, inhibits or preferably inactivates the first foreign DNA or any first RNA, protein or polypeptide expressed in such cells, particularly where the first RNA, protein or polypeptide would kill or adversely disturb significantly the metabolism, functioning or development of such cells. Second foreign DNAs preferably encode, for example, the following: barstar neutralizes the activity of barnase (which degrades RNA molecules by hydrolyzing the bond after any guanine residue); EcoRI methylase which prevents the activity of the endonuclease EcoRI; or a protease inhibitor which nuetralizes the activity of a protease, such as a papain (e.g., papain zymogen and papain active protein). Another preferred example of a second foreign DNA encodes a strand of an antisense second RNA (as described, for example, in EP 223 399) which would be complementary to a strand of a sense first RNA.

In the first and second chimaeric genes of this invention, the 3' transcription termination signals or 3' ends can be selected from among those which are capable of providing correct transcription termination and polyadenylation of mRNA in plant cells. The transcription termination signals can be the natural ones of the first and second foreign DNAs, to be transcribed, or can be foreign. Examples of foreign 3' transcription termination signals are those of the octopine synthase gene (Gielen et al, 1984), and of the T-DNA gene 7 (Velten and Schell, 1985).

The genome of a cell of a plant, particularly a plant capable of being infected with Agrobacterium, can be transformed using a vector that is a disarmed Ti-plasmid containing the first chimaeric gene and optionally the second chimaeric gene of this invention and carried by Agrobacterium. This transformation can be carried out using the procedures described, for example, in EP 116,718 EP 270,822 and Gould et al (1991). Pre-ferred Ti-plasmid vectors contain the first and second chimaeric genes between the border sequences, or at least located to the left of the right border sequence, of the T-DNA of the Ti-plasmid. Of course, other types of vectors can be used to transform the plant cell, using procedures such as direct gene transfer (as described, for example, in EP 233,247), pollen mediated transformation (as described, for example, in EP 270,356, PCT publication WO 85/01856, and U.S. Pat. No. 4,684,611), plant RNA virus-mediated transformation (as described, for example, in EP 67,553 and U.S. Pat. No. 4,407,956) and liposome-mediated transformation (as described, for example, in U.S. Pat. No. 4,536,475). In case the plant to be transformed is corn, it is preferred that more recently developed methods be used such as, for example, the method described for certain lines of corn by Fromm et al (1990) and Gordon-Kamm et al (1990) and the method for cereals described in PCT patent publication WO 92/09696. The resulting transformed plant cell can then be used to regenerate a transformed plant in a conventional manner.

It is preferred that the first and second chimaeric genes of this invention be inserted in the same genetic locus in a plant genome, preferably in a configuration where interference is minimized between cis-acting elements of the fungus-responsive and second promoters. Therefore, it is preferred that the first and second chimaeric genes be transferred to the plant genome as a single piece of DNA, so as to lead to their insertion in a single locus in the genome of the plant. However, plants containing the two chimaeric genes can also be obtained in the following ways:
1. The chimaeric genes can be separately transferred to the nuclear genomes of separate plants in independent transformation events and can subsequently be combined in a single plant genome through crosses.
2. The chimaeric genes can be separately transferred to the genome of a single plant in the same transformation procedure leading to the insertion of the respective chimaeric genes at multiple loci (co-transformation).
3. One of the two chimaeric genes can be transferred to the genome of a plant already transformed with the other chimaeric gene.

Preferably, the first and second chimaeric genes are each inserted into a plant cell genome in the same genetic locus as a conventional chimaeric marker gene. The chimaeric marker gene can suitably comprise a marker DNA that is: under the control of, and fused at its 5' end to, a third plant-expressible promoter, such as one of the constitutive promoters which can be used as the second promoter; and fused at its 3' end to suitable plant transcription termination signals, such as those which can be used in the first or second chimaeric gene. The marker DNA preferably encodes a third RNA and/or protein or polypeptide which, when expressed in cells of a plant, allows such cells to be readily separated from cells in which the third RNA, protein or polypeptide is not expressed. If the first and second chimaeric genes are separately transferred to a plant cell genome, each chimaeric gene is preferably transferred together with a chimaeric marker gene. The choice of the marker DNA is not critical, and a suitable marker DNA can be selected in a well known manner. For example, a marker DNA can encode a protein that provides a distinguishable color to transformed plant cells, such as the A1 gene encoding dihydroquercetin-4-reductase (Meyer et al, 1987), or can provide an antibiotic resistance to transformed plant cells, such as the neo gene encoding resistance to kanamycin (EP 131 623).

The coding region of the first and second chimaeric genes, as well as that of the chimaeric marker gene, can, of course, each comprise naturally occurring DNA or a synthetic or artificial DNA sequence, e.g., in order to obtain increased expression levels in plants. Such an artificial DNA preferably encodes substantially the same protein with substantially the same properties as the protein encoded by the corresponding naturally occurring DNA.

The resulting transformed plant can be used in a conventional breeding scheme to produce more transformed plants with the same characteristics or to introduce the first chimaeric gene and optionally the second chimaeric gene in other varieties of the same or related plant species. Seeds obtained from the transformed plants contain the chimaeric gene(s) of this invention as a stable genomic insert.

The following Examples describe the isolation and characterization of promoter-effective portions of the fragment of the fungus-responsive promoter of the prp1-1 gene of SEQ ID no. 1 and the use of such promoter-effective portions for providing fungus-resistant plants. Unless stated otherwise in the Examples, all nucleic acid manipulations are done by the standard procedures described in Sambrook et al, *Molecular Cloning: A Laboratory Manual*, Second Edition, Cold Spring Harbor Laboratory Press, NY (1989).

In the following Examples, reference is made to the following Drawings and Sequence Listing.

DETAILED DESCRIPTION OF THE DRAWINGS

FIG. 1: Accumulation pattern of PRP1 mRNA in response to different abiotic stimuli in Example 1. Leaves of non-transformed potato cultivar Datura were harvested at the indicated times after initiation of treatment. Panel A shows stimulation with fungal culture filtrate. Panel B shows stimulation by mechanical wounding ("c" is a control indicating the ratio between PAL and PRP1 mRNA in a compatible interaction 36 h after inoculation of leaves from potato cultivar Datura with fungal spores). Panel C shows response to white light after dark-adaptation of plants. Panel D shows heat treatment of leaves at 40° C. (Rec. is recovery at 18° C.). In each panel, 20 µg total RNA were loaded per lane and hybridized with DNA probes for PRP1 and PAL or antisense RNA for HSP70 as marked on the left of each panel. The length of the corresponding transcripts is given on the right of each panel.

Figure 2B:
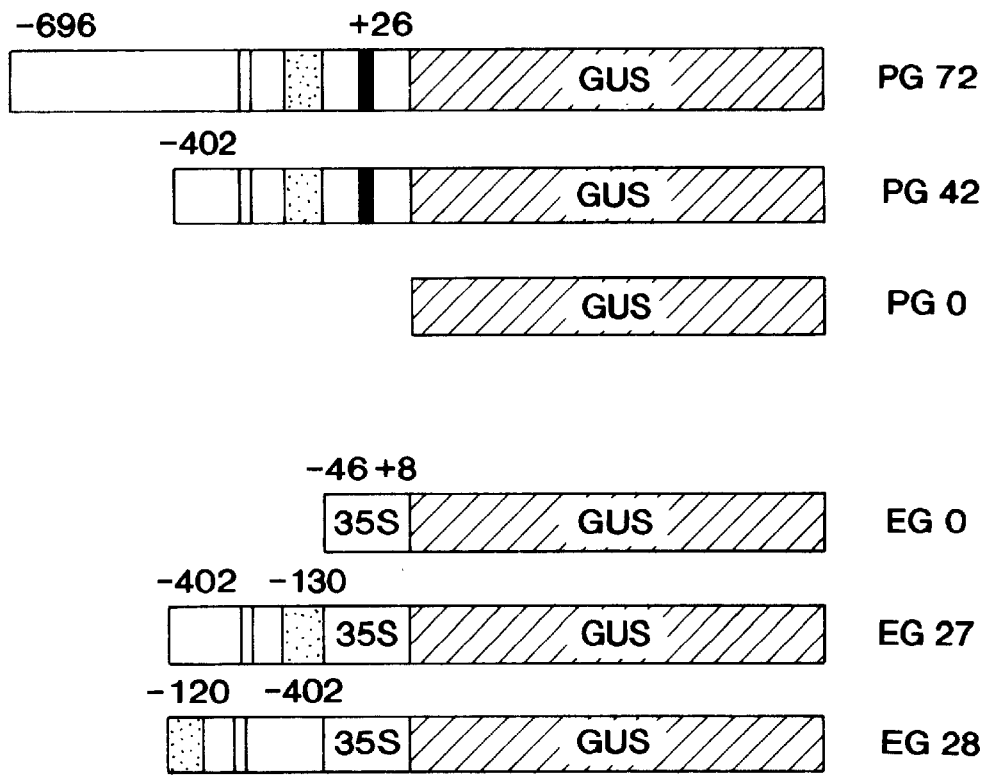

FIG. 2: Schematic drawings of vectors and their DNA inserts, used in Example 2. Panel A shows promoter and enhancer test vectors, pPTVgus and pETVgus; and Panel B shows different DNA inserts comprising portions of the prp1-1 promoter, the 35S promoter and/or the GUS gene between EcoRI and XbaI cleavage sites (underlined) in the multiple cloning regions of pPTVgus and pETVgus. In Panel A, all indicated cleavage sites in pPTVgus and pETVgus for restriction endonucleases, except PstI and SalI, are unique; $Ap^r/Cb^r$ represents a gene for ampicillin and carbenicillin resistance; GUS is *E. coli* uidA gene encoding β-glucuronidase; HPT is hygromycin phosphotransferase gene; LB and RB are left and right T-DNA borders, respectively; P35S is CaMV 35S gene TATA-box region (position −46 to +8); $pA_{3C}$ and $pA_{nos}$ are polyadenylation signals of the pea rbcS-3C and the Agrobacterium nopaline synthase gene, respectively; Pnos is the nopaline synthase promoter; $ori_{Co(E}T$ is the origin of replication of plasmid ColE1; $ori_T$ is the origin of conjugative Ti-plasmid transfer; and $ori_V$ is the origin of Ti-plasmid replication. The end points of the portions of the prp1-1 promoter, inserted in pPTVgus and pETVgus and used to control the expression of the GUS gene, are marked in Panel B ("−696" is at nucleotide 1 in SEQ ID no. 1; and "−402" is at nucleotide 295 in SEQ ID no. 1). PG0 and EG0 in panel B represent control inserts in pPTVgus and pETVgus, without portions of the prp1-1 promoter. In the prp1-1 promoter fragments of Panel B, a vertical bar indicates the putative prp1-1 TATA box.

Figure 3A:
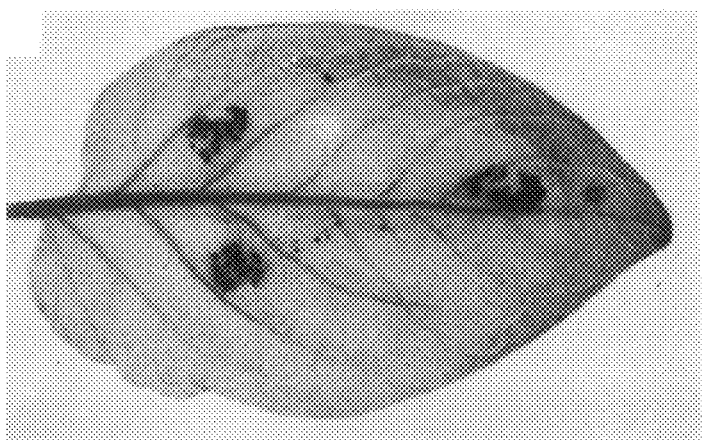
FIGS. 3A–3B depict the histological localization of GUS activity in leaves of EG27 transformations.
Figure 3B:
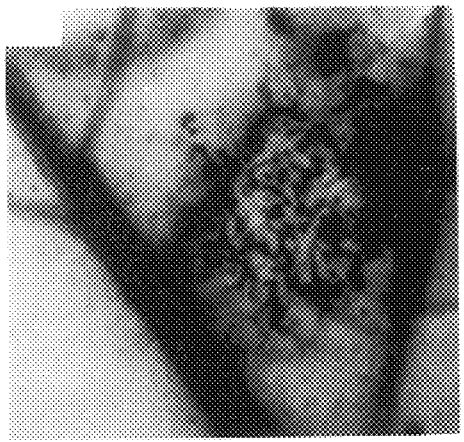

FIG. 3: Histochemical localization of GUS activity in leaves of EG27 transformants 48 h after inoculation with *Phytophthora infestans* race 4 in Example 2. Tissue expressing GUS is recognized by blue indigo dye deposits after staining of leaves with X-GLUC and clearing of pigment with ethanol. Panel A is an overview of a drop-infected leaflet, and Panel B is an enlargement of a necrotic inoculation site.

FIG. 4: Transcript accumulation in individual transformants after infection with *P. infestans* (compatible interaction) in Example 2. RNA was isolated from leaves 48 h after treatment with water (w) or 48 h postinoculation with fungal spores (c). 20 μg total RNA were loaded per lane and hybridized with DNA probes specific for GUS of PRP1 mRNA. Panel A shows RNA from independent transformants of the PG42 series. Panel B shows RNA from independent transformants of the EG27 series. Panel C shows RNA from a PG42 plant, PG4201, and from an EG27 plant, EG2706, isolated at the indicated times postinoculation.

SEQUENCE LISTING

SEQ ID no. 1: DNA sequence of fungus-responsive potato gene, prp1-1, and a fragment of its promoter from nucleotides 1 to 1972. The prp1-1 promoter fragment extends from nucleotide 1 to nucleotide 696.

EXAMPLE 1

Example Analysis of the prp1 Gene Family

The transcript accumulation deriving from a prp1 gene upon stimulation by various environmental signals was analyzed by RNA-blot hybridization experiments. Leaves of potato cultivar Datura were drop-inoculated with spore suspensions of *P. infestans* race 1 or 4 resulting in compatible (host susceptible/fungus virulent) or incompatible (host resistant/fungus avirulent) interactions. Changes in the steady state level of PRP1 mRNA during the course of infection were measured in parallel with the accumulation of mRNA encoding another defense-related protein, phenylalanine ammonia lyase ("PAL"). An increase of PRP1 mRNA concentration could already be detected 4 h postinoculation in a compatible interaction; the maximum transcript level is reached 24–36 h postinoculation. In an incompatible interaction, the accumulation of PRP1 mRNA is first detectable 12–18 h postinoculation but also reaches its maximum about 24 h postinoculation; the absolute amount of PRP1 mRNA present in incompatible interactions is significantly lower than in compatible interactions. The profile of PAL mRNA steady state levels during the time course of infections parallels that found for PRP1 mRNA (Taylor et al, 1990). As indicated in FIG. 1A, the PRP1 mRNA transcript level also increases upon incubation of potato leaves with culture filtrate elicitor from *P. infestans.*

In order to test the response of prp1 genes to different abiotic environmental stimuli, mRNA accumulation patterns after wounding and illumination with white light were analyzed. No significant change in PRP1 mRNA concentration was observed upon mechanical injury of leaves while the amount of mRNA hybridizing with a pal-specific probe increased rapidly and transiently under these conditions (FIG. 1B). Similarly, the PRP1 mRNA concentration stayed at a low level during a 72 h period of dark-adaptation of potato leaves and during subsequent illumination of these leaves with white light for 48 h, but the amount of PAL mRNA decreased during such a dark-adaptation period and then increased when the plant was exposed to white light (FIG. 1C).

Because of the structural similarity between the coding regions of the prp1-1 gene and the soybean hsp26 gene, as well as the presence of a heat shock element-like sequence in the prp1-1 promoter, the impact of heat treatment on the expression of the prp1 gene family in leaves of potato cultivar Datura was also tested. At a temperature of 39° C., which led to a rapid and transient accumulation of transcripts homologous with maize Hsp70 RNA, no obvious response of the prp1 gene was detected in RNA-blot hybridization experiments (FIG. 10).

The comparatively specific PRP1 mRNA accumulation upon fungal infection would appear to make the prp1-1 gene, as well as other members of the prp1 gene family, ideal candidates to provide cis-acting elements which can provide transcriptional activation in potato during the development of late blight disease.

EXAMPLE 2

Isolation and Characterization of the Promoter Regions of the Fungus-responsive prp1-1 Gene Plants of the potato cultivars Datura and Désirée (*Solanum tuberosum* L, carrying resistance genes R1 and R0, respectively) were grown in soil for 6 weeks in the greenhouse with a 16 hour/day light period at 18° C. Mature detached leaves of these plants were inoculated from the abaxial side with 15 to 20 drops of either a 20 μl aqueous spore suspension ($10^4$ spores) from *Phytophthora infestans* race 4 or distilled water and were then placed into vials containing sterile tap water; in-cubation was carried out in small growth chambers at 70% relative humidity and 18° C. under a 16 h/18 h light/dark regime. After different times, inoculation sites were punched out with a cork borer and frozen in liquid nitrogen.

The PRP1-1 cDNA clone was isolated as described by Taylor et al (1990). In order to isolate the genomic DNA clones carrying the regulatory sequences of the genes corresponding to the PRP1-1 cDNA clone, a genomic library was constructed from potato cv. Datura DNA. The fungus-responsive PRP1-1 cDNA was used as a probe for screening the library. Three genomic clones were isolated. Two of them appeared to be identical. Regions hybridizing with PRP1-1 cDNA or end-labeled mRNA, which detected 5' portions not present on the cDNA, were identified and sequenced. At the 5' end of the homologous region of each genomic clone, the ATG translation initiation codon and TATA consensus sequence were identified in order to locate the fungus-responsive promoter region.

Promoter and enhancer test vectors, pPTVgus and pETVgus, of FIG. 2 were constructed, containing the *E. coli* uidA gene (gus) as a reporter gene (Jefferson et al, 1987). A 450 bp XhoI/ApaI fragment close to the right T-DNA border in vector pPCV811 (Koncz et al, 1989) was deleted thereby removing one of two BstEII sites. The SalI/BstEII fragment of this modified vector was replaced by a SalI/EcoRI fragment of plasmid pBI101, containing gus (Jefferson et al, 1987), thereby creating pPTVgus (FIG. 2).

For construction of enhancer test vector pETVgus, the BglII/BstEII fragment of the modified plasmid pPCV811 was replaced by a BglII/EcoRI fragment covering the CaMV 35S TATA box region (position −46 to +8), the GUS-encoding gene and the pea rbcS-3C 3'-end (Benfey and Chua, 1990). The 5'-flanking region of prp1-1, contained in the genomic clone Lambda St128 (Taylor et al, 1990), was excised as a 722 bp long EcoRI/StyI fragment and subcloned into EcoRI-and SmaI-digested plasmid pBS(+) (Stratagene, La Jolla, USA); the StyI site of the insert was maintained in a blunt end ligation with the SmaI site of the vector. This cloning step yielded intermediate plasmid pBS72-1. Sau3AI cleavage of the EcoRI/BamHI fragment from this plasmid resulted in a 428 bp Sau3AI/BamHI subfragment; this fragment was inserted into vector pBS(+) via BamHI, yielding intermediate plasmids pBS42-1 and pBS42-2 (two possible orientations). These two plasmids were used for Bal3I treatment of the prp1-1 inserts, starting from the genomic 3'-end in order to remove the putative TATA box sequence. First, pBS4201 and pBS42-2 were cleaved with XbaI and EcoRI, respectively, after treatment with Bal31 and addition of XbaI or EcoRI linkers, and the subsequent religation resulted in plasmids pBS27-1 and pBS28-2. The prp1-1 promoter regions in plasmids pBS27-1 and pBS42-1 were excised as EcoRI/XbaI fragments and ligated into the EcoRI/XbaI-digested promoter test vector pPTVgus (FIG. 2) to give transcriptional prp1-1/gus-gene fusion plasmids pPTVgus72-1 and pPTVgus42-1, respectively, harboring constructs PG72 and PG42. The EcoRI/XbaI fragments of plasmids pBS27-1 and pBS28-2 were inserted into the appropriate polylinker sites 5'terminal of the CaMV 35S TATA box region in the enhancer test vector pETVgus (FIG. 2) to give plasmids pETVgus27-1 and pETVgus28-2, respectively, containing constructs EG27 and EG28.

The resulting chimaeric constructs were transferred into potato cultivar Désirée (R0). In this regard, plasmids for plant transformation were mobilized from *E. coli* strain S17-1 to *Agrobacterium tumefaciens* strain C58Cl-GV3101 harboring the helper plasmid pMP90RK (Koncz et al, 1989).

The capacity of the different promoter fragments to confer transcriptional activation was then measured in transformed Désirée leaves after treatment with water (control) and after inoculation with spore suspensions of *P. infestans* race 4, resulting in a compatible interaction. First, the expression pattern was assayed at the level of GUS activity. A population of 6–10 independent transformants was tested per construct; from each plant, three mature leaves were inoculated, finally yielding 60 inoculation sites in total. All constructs revealed only low GUS activity upon treatment of leaves with water; however, an up to 6-fold and an up to 18-fold higher GUS activity were found in leaves of PG42- and EG27-plants, respectively, 48 h after inoculation with fungal spores (Table 1). A slight inducibility of GUS activity was also observed in some transformants harboring construct EG28. In plants containing constructs PG72, PG0 or EG0, GUS activity stayed at the level of water treatment upon fungal infection (Table 1). Southern hybridization experiments with genomic DNA proved that all these plants had indeed been transformed.

The spatial pattern of GUS activation in plants carrying the EG27 construct was determined by histochemical analysis of the most active representative (EG2706). Infected leaflets were infiltrated with a solution containing the GUS substrate X-GLUC. 48 h postinoculation, GUS activity was detectable within, and in the close vicinity of, necrotic inoculation sites indicated by blue staining (FIG. 3). In infected leaves from transgenic plants of the EG0 series, no staining of inoculation sites was observed, thereby proving that GUS activity in leaflets of the EG27 representative did not originate from the fungus.

The inducible transcription of constructs PG42 and EG27 was also tested on the level of mRNA accumulation. Total RNA from leaves of the corresponding plants, either inoculated with fungal spores or treated with water, was hybridized with probes specific for GUS or PRP1 mRNA. FIG. 4 shows the results of these Northern hybridization experiments. In all dependent transformants of the PG42 series and five of seven transformants of the EG27 series, the PRP1 and GUS transcript levels increased within 48 h after inoculation of leaves with spores of *P. infestans* race 4; the significantly higher absolute amounts of PRP1 mRNA are believed to be due to the higher copy number of prp1 genes as compared to the chimaeric constructs (i.e., 10–15 versus 1–2). Control constructs PG0 and EG0 did not lead to a detectable level of GUS mRNA either in the uninduced or the induced state.

In order to determine the time course of transcriptional activation conferred by constructs PG42 and EG27, the transcript accumulation of individual transformants (PG4201 and EG2706) was followed starting at an early time point postinoculation (FIG. 4C). GUS mRNA was first detected 2 h postinoculation, and the transcript level steadily increased until 48 h postino-culation. Qualitatively, the kinetics of GUS and PRP1 mRNA accumulation during infection are very similar (FIG. 4C).

GUS, Northern blot and histochemical analysis confirmed that the 273bp-35S promoter fragment (in EG27 plants) was not activated upon wounding, $CdCl_2$-treatment, heat shock (1 hr at 40° C.) and illumination with white light (5200 lux). By comparison, PAL expression was shown to be induced by wounding and illumination of dark-adapted leaves with white light, and the native prp1-1 promoter showed induction after $CdCl_2$-treatment. Only fungal infection, fungal elicitor preparations, salicylic acid (0.1 mM, 4 hrs after onset of experiment), and to a much lesser extent cytokinin and indole-3-acetic acid (both 6 hr, 50 µM) were capable of inducing a response by the 273bp-35S promoter in potato plants. The response to fungal infection was rapid and strictly localized, the only activity in non-infected tissue was found in the root tips. Since many healthy regenerants were obtained in the plants with a constitutively expressed barstar gene, the expression in root tips of barnase was not found to disturb significantly plant regeneration and growth. Besides *Phytophtora infestans,* the non-pathogenic fungus for potato, *Cladosporium fulyum,* was found to induce transcriptional activation by the 273bp-35S promoter fragment in potato.

These results indicate that the prp1-1 5'-terminal sequence between positions 295 and 567 in SEQ ID no. 1 comprises cis-acting elements sufficient for rapid and strictly localized transcriptional activation in compatible and incompatible interations of potato with *P. infestans* and other fungi. This function is maintained, and the specificity is even increased, after combination of the promoter segment with a heterologous TATA box region from the CaMV 35S sequence between position −46 and +8. However, on average, construct PG42 conferred a higher overall GUS activity and mRNA level before stimulation by pathogen attack then did construct EG27. Surprisingly, addition of prp1-1 upstream sequences between positions 1 and 294 in SEQ ID no. 1 (construct PG72) blocks the transcriptional activation upon fungal infection, suggesting the presence of negatively cis-acting elements in that region.

EXAMPLE 3

Construction of Plant Transformation Vectors

As described in detail below, the two promoter fragments derived from the prp1-1 gene in Example 2 were used to construct first chimaeric genes of this invention which were then used with second chimaeric genes of this invention to construct plant transformation vectors. One prp1-1 promoter fragment consists of a 428 bp fragment of the 5' region of the prp1-1 gene, from nucleotide 295 to nucleotide 722 in SEQ ID no. 1, and the other prp1-1 promoter fragment consists of 273 bp of the 5' region of the prp1-1 gene from nucleotide 295 to nucleotide 567 in SEQ ID no. 1 and a minimum CaMV 35S promoter fragment from nucleotide −46 to nucleotide +8 of the CaMV 35S promoter (Benfey et al, 1990a, b). Each of the promoter fragments is upstream of, and in the same transcriptional unit as, a first foreign DNA encoding barnase from *Bacillus amyloliquefaciens* (Hartley, 1988). Downstream of the first foreign DNA is the 3' untranslated end of the nopaline synthase gene ("3'nos") which has been isolated as a 260 bp TaqI fragment from the nopaline synthase gene (Gielen et al, 1984). This resulted in two chimaeric gene constructs that were designated "pPRP1-barnase-3'nos" and "pPRP1/35S-barnase-3'nos". These first chimaeric genes were introduced between the T-DNA border repeats of a vector, pGV941, suitable for plant transformations as described by Deblaere et al (1987). This vector contains a chimaeric marker gene containing the noplaine synthase promoter ("pnos"; Depicker et al, 1982), the neo coding region from Tn5 (Beck et al, 1982) and the 3' untranslated end of the octopine synthase gene ("3'ocs"), corresponding to the 706 bp PvuII fragment from the octopine synthase gene (Gielen et al, 1984). The construction of this chimaeric "pnos-neo-3'ocs" gene has been described by Hain et al (1985) and in EP 359 617.

The first chimaeric genes also were introduced within the T-DNA vector, pGV941, together with a second chimaeric gene of this invention as described in detail below. The second chimaeric gene contains the CaMV 35S promoter (EP 359 617) fused to the barstar coding region (Hartley, 1988) and the 3' untranslated end of the T-DNA gene 7 (3'g7) carrying signals for transcription termination and polyadenylation (Velten and Schell, 1985).

The construction of the first chimaeric genes of this invention, containing a barnase gene, was as follows. An intermediate plasmid vector, pCV3, was constructed containing a chimaeric PTA29-barnase-3'nos gene construct cloned in the polylinker region of pGEM2 (Promega, Madison, Wis. USA). A construct, pTTM8, carrying the barnase coding region under the control of the tobacco tapetal specific promoter, TPA29, has been described in EP 344 029. The PTA 29-barnase fragment was retrieved as an EcoRI fragment from pTTM8 and inserted in the pGEM2 polylinker. To prevent expression of the barnase gene as directed from the TA29-barnase fragment cloned within the vector, a barstar gene was also cloned in the polylinker region of pGEM2. In this way, potential lethal effects in bacterial hosts caused by expression of the barnase-encoding DNA fragment within a microbial host is avoided. The barstar gene under control of its own promoter was obtained as an XbaI fragment from pMT416 (Hartley, 1988). The cloning of both fragments in the polylinker region was designed in such a way that the TA29 promoter fragment could be easily replaced by a prp1-1 promoter fragment, using the unique EcoRI site localized at the 5' end of the promoter region and NcoI site overlapping with the ATG initiation codon of the barnase coding region. PRP1-1 and PRP1-1/35S promoter fragments were isolated from the plasmids pBS42-1 and pETVGUS27-1 (from Example 2) as respectively a XbaI/EcoRI fragment and a HindIII/EcoRI fragment. For ligation, the XbaI and HindIII 5'-protruding ends were filled in with Klenow DNA polymerase and ligated to the Klenow filled NcoI ends at the ATG codon of the barnase coding region. This yielded respectively: the plasmid "pCV4" carrying the pPRP1-barnase-3'nos first chimaeric gene construct and the plasmid pCV11 carrying the pPRP1/35S-barnase-3'nos first chimaeric gene construct.

T-DNA plant transformation vectors containing the above-described first chimaeric genes of this invention, chimaeric marker gene and optional second chimaeric gene of this invention were constructed as follows. Each first chimaeric gene was retrieved as an EcoRI/HindIII fragment and cloned within the T-DNA vector, pTTM8 (EP 344 029). In order to obtain a T-DNA vector carrying the first chimaeric gene constructs, pTTM8 was digested with EcoRI and SnaBI to remove its chimaeric barnase gene and sfr gene (EP 242 236) constructs. Cloning of the respective first chimaeric gene constructs in the pTTM8 vector yielded the T-DNA vectors, pTCV13 and pTCV14. These vectors contain a chimaeric neo gene (pnos-neo-3'ocs) and a chimaeric barnase gene (pPRP1-barnase-3'nos or pPRP1/35S-barnase-3'nos, respectively) cloned between the terminal border repeats of the T-DNA.

In order to construct T-DNA plant transformation vectors carrying also second chimaeric genes of the invention, a DNA fragment containing a CaMV35S-barstar-3'g7 gene construct was introduced in pTCV13 and pTCV14. In this regard, the CaMV35S-barstar-3'g7 chimaeric gene was constructed as follows, starting from a construct carrying the barstar gene as described in EP 412 911. A Cla1 site was introduced at the ATG codon of this construct by site-directed mutagenesis (EP 319 353). The barstar gene was then isolated as a Cla1/HindIII fragment from the resulting construct. The barstar gene fragment was ligated at its 5' end to a CaMV 35S promoter fragment and provided with signals for transcription termination and polyadenylation from the T-DNA gene 7. To this end, the Cla1/HindIII barstar gene fragment was cloned in the vector pGSJ280 (Deblaere et al, 1987), digested with ClA1 and BamHI. For ligation, the BamHI and HindIII protruding ends were filled in by Klenow DNA polymerase. The resulting plasmid, pTTM7, carries the chimaeric CaMV35S-barstar-3'g7 gene construct which was retrieved as a ScaI/SnaBI fragment, with the ScaI site localized at the 5' end of the CaMV 35S promoter of the fragment and the SnaBI site localized downstream from the 3'g7 of the fragment. This fragment was treated with Klenow DNA polymerase and cloned within the blunted EcoRI site of pTCV13 and pTCV14, this site being localized between the two chimaeric genes of the T-DNA region. This yielded the T-DNA vectors, pTCV15 and pTCV16, which carry three chimaeric genes between the T-DNA border repeats, pnos- neo-3'ocs, CaMV35S-barstar-3'g7 and pPRP1-barnase-3'nos or pPRP1/35S-barnase-3'nos. The vector pTCV17 is similar to pTCV16, except that the chimaeric gene CaMV35S-barstar-3'g7 has the opposite orientation, and has the 35S promoter further away from the prp1-35S promoter fragment. pTCV1 is a control vector, containing the prp1-gus-3'nos and the pnos-neo-3'ocs constructs. This vector is identical to the pPTV gus vector of FIG. 2, except that the hygromycin resistance gene has been replaced with a chimaeric neo gene.

Using the procedure described above, a plant transformation vector is also constructed containing a first chimaeric gene, designated "prp1-3-lectin-3'nos", using the lectin from Broeckaert et al. (1989).

EXAMPLE 4

Transformation of Potato and Oilseed Rape with *Agrobacterium tumefaciens* Strains Carrying the Plant Transformation Vectors of Example 3

To obtain transformation of, and major expression in, potato and oilseed rape (*Brassica napus*), the plant transformation vectors of Example 3 are each mobilized into the Agrobacterium tumefaciens strain C57ClRif$^R$ carrying the avirulent Ti plasmid pGV2260 as described by Deblaere et al (1985). The transconjugants are analyzed by Southern blotting. The respective Agrobacterium strains are used to transform potato plants (Solanum tuberosum cvs. Bintje and Desireé) by means of tuber disc infection as described by De Block et al (1987) and oilseed rape using the method described by De Block et al (1989). Transformed calli are selected on medium contained 100 μg/ml kanamycin, and resistant calli are regenerated into plants. For each transformation experiment, about 10 individual transformants are regenerated and analyzed by Southern blotting for gene integration patterns.

Plants transformed with the fungus-responsive first chimaeric genes of this invention, containing the fungus-responsive prp1-1 promoter fragments of Example 2, show a significantly higher degree of resistance to fungus infection, particularly Phytophthora infestans infection, than do non-transformed control plants. As a result, the transformed plants have significantly lower yield losses than do the control plants.

Certain plants transformed with a vector containing both the barnase chimaeric gene and the barstar chimaeric gene (plants DST 22-6 and DST 9-3) performed significantly better than all others upon fungal infection (Table 2). Leaves of these lines showed a significant delay in the onset of symptoms of fungal infection, particularly in sporulation and in spread of sites of infection, after being inoculated with Phytophtora infestans (race 1). When compared to control plants, fungal sporulation was significantly inhibited even 7 days after infection. Sporulation was followed by examination under the stereoscope, after fungal infection, by applying 20 μl droplets (when using either $2 \times 10^6$ to $5 \times 10^5$ spores/ml) to the bottom side of the potato leaf. After maintenance of the leaves in water, the fungal growth and sporulation could be followed by visual inspection under a stereoscope. In leaves of line 9-3, the necrotizing 'browning' zone was found to be spreading slower then in either non-transformed control plants or control plants containing the chimaeric prp1-1-gus gene. The transformed Bintje plants of the invention, expressing barnase substantially specifically at the site of fungal infection, clearly show a significantly higher resistance to fungal infection when compared to non-transformed plants. The disease resistance phenotype is confirmed by molecular analysis based on RNA quantification and evaluation of the phenotype in the segregating progeny.

Needless to say, the use of the fungus-responsive promoters and chimaeric genes of this invention is not limited to the transformation of any specific plant(s). Such promoters and chimaeric genes can be useful in transforming any crop, such as alfalfa, corn, cotton, sugar beet, brassica vegetables, tomato, soybean, wheat or tobacco, where the promoters can control gene expression, preferably where such expression is to occur abundantly in plant cells which immediately surround fungal infection sites.

Also, the use of the fungus-responsive promoters of this invention is not limited to the control of particular first foreign DNAs but can be used to control expression of any foreign gene or DNA fragment in a plant.

Furthermore, this invention is not limited to the specific fungus-responsive prp1-1 promoter and promoter fragments described in the foregoing Examples. Rather, this invention encompasses promoters and promoter fragments, equivalent to those of the Examples, such as other prp1promoters, which can be used to control the expression of a structural gene, such as a first foreign DNA, at least substantially selectively in plant cells which immediately surround a fungal infection site. Indeed, it is believed that the DNA sequences of the prp1-1 promoter and promoter fragments of the Examples can be modified by replacing some of their nucleotides with other nucleotides, provided that such modifications do not alter substantially the ability of polymerase complexes, including transcription activators, of plant cells which immediately surround the fungal infection site to recognize the promoters, as modified.

Nor is this invention limited to the use of the fungus-responsive chimaeric genes of this invention for protecting plants against a Phytophthora such as P. infestans. Such chimaeric genes can be used to protect plants against plant-pathogenic fungi, generally, particularly against Phytophthora spp, Pythium spp, Fusarium spp, Sclerotinia spp, Puccinia spp, Ustilago spp, Alternaria spp, Helminthosproium spp, Sclerotinia sclerotiorum, Pyrebioeriza brassicae, Cylindrosporium concentricum, Phoma lingam and Leptosphaeria maculans.

TABLE 1

Expression of prol-1/uidA transcriptional fusions in transgenic potato cultivar Desiree

| Transformant | | GUS activity water | (pMol MU/min/mg protein)* fungal spores | Fold Induction |
|---|---|---|---|---|
| PG 0 | 01 | 3.3 | 3.8 | 1.1 |
| | 02 | 3.0 | 3.3 | 1.1 |
| | 04 | 4.3 | 3.2 | — |
| | 05 | 3.6 | 3.2 | — |
| | 06 | 3.3 | 5.8 | 1.8 |
| | 09 | 6.7 | 2.9 | — |
| PG 42 | 01 | 9.4 | 39.1 | 4.2 |
| | 03 | 17.1 | 44.8 | 2.6 |
| | 04 | 6.2 | 36.8 | 5.9 |
| | 05 | 28.7 | 102.9 | 3.6 |
| | 06 | 17.5 | 68.5 | 3.9 |
| | 07 | 7.7 | 39.0 | 5.1 |
| | 08 | 64.4 | 110.1 | 1.7 |
| PG 72 | 02 | 6.5 | 10.2 | 1.6 |
| | 02 | 5.1 | 6.9 | 1.4 |
| | 04 | 3.4 | 4.7 | 1.4 |
| | 05 | 10.6 | 7.4 | — |
| | 06 | 3.8 | 4.8 | 1.3 |
| | 07 | 6.5 | 7.6 | 1.2 |
| | 08 | 3.7 | 5.8 | 1.6 |
| | 09 | 5.8 | 6.5 | 1.1 |
| | 10 | 4.7 | 7.3 | 1.6 |
| | 11 | 8.2 | 8.2 | — |
| EG 0 | 02 | 4.1 | 3.6 | — |
| | 05 | 3.8 | 3.3 | — |
| | 06 | 3.7 | 3.5 | — |
| | 07 | 4.6 | 3.8 | — |
| | 08 | 4.5 | 3.1 | — |
| | 09 | 5.0 | 3.7 | — |
| EG 27 | 01 | 10.6 | 184.7 | 17.4 |
| | 03 | 4.0 | 6.5 | 1.6 |
| | 05 | 6.3 | 61.8 | 9.8 |
| | 06 | 8.1 | 143.4 | 17.7 |
| | 08 | 5.0 | 15.9 | 3.2 |
| | 09 | 2.8 | 7.1 | 2.5 |
| | 10 | 3.1 | 21.8 | 7.0 |
| EG 28 | 03 | 8.0 | 13.9 | 1.7 |
| | 04 | 13.8 | 24.7 | 1.8 |
| | 05 | 6.8 | 17.3 | 2.5 |
| | 06 | 5.1 | 21.5 | 4.2 |
| | 07 | 4.7 | 3.0 | — |
| | 08 | 4.6 | 3.1 | — |
| | 09 | 5.9 | 12.2 | 2.1 |

*48 h after onset of treatment: mean values of two to four independent infections

TABLE 2

| plants[a] | SPORULATION: days postinculation | | | | | | |
|---|---|---|---|---|---|---|---|
| | 1 | 2 | 3 | 4 | 5 | 6 | 7 |
| DST 2-3 | 0 | 0 | 0 | 1 | 2 | 2/3 | 3 |
| DST 23-1 | 0 | 0 | 0 | 0 | 1≠ | 2≠ | 3 |
| DST 23-6 | 0 | 0 | 0 | 1 | 1 | 2/3 | 3 |
| DST 9-1 | 0 | 0 | 0 | 1/2 | 3 | 3 | 3 |
| DST 9-3 | 0 | 0 | 0 | 0* | 0/1* | 1* | 0/1* |
| DST 22-3 | 0 | 0 | 0 | 0/1 | 2 | 3 | 3 |
| DST 22-6 | 0 | 0 | 0 | 0§ | 1§ | 2 | 2/3 |
| Isola (R4) | 0 | 0 | 0 | 0 | 0 | 0 | 0 |

Legend to Table 2:
[a]plants: DST 2-3 is a kanamycin-resistant (Km+) plant of the pTCV1 transformation event. DST 23-1 and 23-6 are respectively Km+ and kanamycin-susceptible (Km−) plants of the pTCV15 event. DST 9-1 and 9-3 are respectively Km− and Km+ plants from the pTCV17 transformation event, and DST 22-3 and 22-6 are respectively Km− and Km+ plants from the pTCV17 event (Km− plants are escapes from the selection assay which can not grow on kanamycin medium, and thus not contain a functional antibiotic resistance gene). Isola is a potato variety naturally resistant to the Phytophtkora infestans race tested.
≠5th day: 9 out of 37 inoculation sites show very slight sporulation at edges
6th day: 5 out of 37 inoculation sites show weak to medium sporulation. 10 out of 37 inoculation sites show medium sporulation
*4th day: 8 out of 62 inoculation site show very slight sporulation at edges
5th day: 6 out of 62 inoculation sites show slight sporulation
6th day: 7 out of 62 inoculation sites show weak sporulation
§4th day: 4 out of 44 inoculation sites show very slight sporulation at edges
5th day: ca. 50% of inoculation sites show slight sporulation (in normal conditions: about 90% of inoculation sites show sporulation)
Rating:
"0": not detectable
"1": weak
"2": medium
"3": strong

REFERENCES

BECK ET AL., Gene 19, 327–336 (1982)
BECKER-ANDRE M., SCHULZE-LEFERT P. and HAHLBROCK K., J. Biol. Chem. 266, 8551–8559 (1991)
BENFEY AND CHUA, Science 250, 959–966 (1990)
BOWLES D. J., Annu. Rev. Biochem. 59, 873–907 (1990)
BROECKAERT W., VAN PARIUS J., LEYNS F., JOOS H. and PEUMANS W., Science 245, 1100–1102 (1989)
COLLINGE D. B. and SLUSARENKO A. J., Plant Mol. Biol. 9, 389–410 (1987)
CZARNECKA E., EDELMAN L., SCHOFFL F. and KEY J. L., Plant Mol. Biol. 3, 45–58 (1984)
DE PICKER ET AL., J. Mol. Appl. Genet. 1, 561 (1982)
DE WIT P. Z., Specificity of Active Resistance Mechanisms in Plant-fungus Interactions, pp. 1–25 in G. Pegg and P. Ayres (Eds.). Fungal Infection of Plants (1987)
DEBLAERE ET AL., Methods in Enzymology 153, 277–292 (1987).
DEBLAERE ET AL., Nucleic Acids Research 153, 272–292 (1985).
DEBLOCK ET AL., EMBO J. 6, 2513–2518 (1987)
DEBLOCK M., DE BROUWER, D. AND TENNING, P., Plant Physiol. 91, 694–701 (1989)
DOUGLAS, D. J., HAUFFE K. D., ITES-MORALES M. E., ELLARD M., PASZKOWSKI U., HAHLBROCK K. AND DANGL J. L., EMBO J., 10, 1767–1775 (1991)
DRON ET AL., Proceedings of the National Academy of Sciences USA 85, 6738–6742 (1988)
DUNSMUIR P., BOND D., LEE K., GIDONI D., TOWNSEND J., Stability of introduced genes and stability in expression, Section CI, pp. 1–17 in Plant Molecular Biology Manual (1988)
FRANCK, GUILLEY, JONARD, RICHARDS and HIRTH, Cell 21, 285–294 (1980)
FRITZEMEIER K. H., CRETIN C., KOMBRINK E., ROHWER F., TAYLOR J., SCHEEL D. and HAHLBROCK K., Transient induction of phenylalanine ammonia-lyase and 4-coumarante: CoA ligase mRNAs in potato leaves infected with virulent or avirulent races of Phytophthora infestans, in Plant Physiol. 85, pp 34–41 (1987)
FROMM M., MORRISH F., ARMSTRONG C., WILLIAMS R., THOMAS J. and KELIN T., Bio/Technology 8, 833–839 (1990)
GARDNER, HOWARD, HAHN, BROWN-LUERT, SHEPARD and MESSING, Nucleic Acids Research 9, 2871–2887 (1981)
GIELEN J., DE BEUCKELEER J., SEURINCK J., DEBOECK F., DE GREVE H., LEMMERS M., VAN MONTAGU M. and SCHELL J., EMBO J. 3, 835–845 (1984)
GORDON-KAMM W., SPENCER M., MANGANO M., ADAMS T., DAINES R., START W., O'BRIEN J., CHAMBERS S., ADAMS W., WILLETS N., RICE T., MACKEY C., KRUEGER R., KAUSCH A. and LEMAUX P., The Plant Cell 2, 603–618 (1990)
GOULD ET AL., Plant Physiology 95, 426–434 (1991)
HAGEN G., UHRHAMMER N. and GUILFOYLE T. J., J. Biol. Chem. 263, 6442–6446 (1988)
HAHLBROCK K. and SCHEEL D., Annu. Rev. Plant Physiol. Plant Mol. Biol. 40, 347–369 (1989)
HAIN ET AL., Mol. Gen. Genet. 199, 161–168 (1985)
HARTLEY ET AL., Journal Mol. Biol. 202, 913–915 (1988).
HARTLEY and ROGERSON, Preparative Biochemistry 2, 243–250 (1972).
HODGE ET AL., Glasgow Symposium, p. 33 (September 1990)
HULL and HOWELL, Virology 86, 482–493 (1987)
JEFFERSON R. A., KAVANAGH T. A. and BEVAN M. W., EMBO J. 6, 3901–3907 (1987)
JOOS H.-J and HAHLBROCK K., Eur. J. Biochem. 204, 622–629 (1992)
KONCZ C., MARTINI N., MAYERHOFER R., KONCZ-KALMAN Z., KORBER H., REDEI G. and SCHELL J., Proc. Natl. Acad. Sci. USA 86, 8467–8471 (1989)
KONCZ and SCHELL, Mol. Gen. Genetics 204, 383–396 (1986)
KRAMER and FRITZ, Methods and Enzymology 154, 350 (1988)
KROMBRINK E., SCHRODER M. and HAHLBROCK K., Proc. Natl. Acad. Sci. USA 85, 782–786 (1988)
LAMB C. J., LAWTON M. A., DRON M. and DIXON R. A., Cell 56, 215–224 (1989)
LAPEYRE B. and AMALRIC F., A powerful method for the preparation of cDNA libraries: Isolation of cDNA encoding a 100-k-Dal nucleolar protein. Gene 37, pp 215–220 (1985)
MEYER ET AL., Nature 330, 677–678 (1987)
OSHIMA M., ITOH H., MATSUOKA M., MURAKAMI T. and OHASHI Y., The Plant Cell 2, 95–106 (1990)
RYANN C. A., Annu. Rev. Phytopathol. 28, 425–449 (1990)
SCHMID J., DOERNER P. W., CLOUSE S. D., DIXON R. A. and LAMB C. J., The Plant Cell 2, 619–631 (1990)

STERMER B. A., SCHMID J., LAMB C. J. and DIXON R. A., Mol. Plant-Microbe Interact. 3, 361–388 (1990)
TAYLOR J. L., FRITZEMEIER K. H., HAUSER I., KOMBRINK E., ROHWER F., SCHRODER M., STRITTMATTER G. and HAHLBROCK K., Mol. Plant-Microbe Interact 3, 72–77 (1990)
VAN LOON L. C., Plant Mol. Biol. 4, 111–116 (1985)
VELTEN J. and SCHELL J., Nuclear Acids Research 13, 6981–6998 (1985)
VELTEN J., VELTEN L., HAIN R. and SCHELL J., EMBO J. 3, 2723–2730 (1984)
VIERLING E., Annu. Rev. Plant Physiol. Plant Mol. Biol. 42, 579–620 (1991)
WARD E. R. ET AL., The Plant Cell 3, 1085–1094 (1991)

What is claimed is:

1. An isolated fungus responsive promoter element obtained by the process comprising the steps of:
   i) identifying a DNA fragment in the genomic DNA of a plant using a DNA fragment consisting of the nucleotide sequence of SEQ ID No. 1 from the nucleotide at position 295 to the nucleotide at position 567 as a hybridization probe and wherein said plant genomic DNA fragment in i) hybridizes to said hybridization probe using the following consecutive steps:
      a) immobilizing plant genomic DNA fragments on a filter;
      b) prehybridizing said filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS;
      c) adding said hybridization probe which has been radiolabeled;
      d) incubating for 16 to 24 hours;
      e) washing said filter for 20 minutes at room temperature in 1×SSC, 0.1% SDS; and
      f) washing said filter three times for 20 minutes each at 68° C. in 0.2×SSC, 0.1SDS; and
      g) autoradiographing said filter by exposing said filter for 24 to 48 hours to X-ray film at −70° C. with an intensifying screen; and
   ii) isolating a DNA fragment of about the same size as said hybridization probe comprising said identified DNA fragment.

2. An isolated fungus responsive promoter comprising the isolated fungus responsive promoter element of claim 1.

3. The fungus responsive promoter of claim 2, wherein said fungus responsive promoter element is operably linked to a heterologous TATA box region from another plant expressible promoter.

4. The fungus responsive promoter of claim 3, wherein said heterologous TATA box region is from a CaMV35S promoter.

5. An isolated fungus responsive promoter comprising a fungus-responsive promoter element with a length of about 273 nucleotides, wherein said fungus-responsive promoter element hybridizes in a conventional manner with a DNA probe consisting of the nucleotide sequence of SEQ ID No. 1 from the nucleotide at position 295 to the nucleotide at position 567 and wherein said conventional hybridization comprises the following consecutive steps:
   a) immobilizing plant genomic DNA fragments on a filter;
   b) prehybridizing said filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS;

c) adding said hybridization probe consisting of the nucleotide sequence of SEQ ID No. 1 from the nucleotide at position 295 to the nucleotide at position 567 which has been radiolabeled;

d) incubating for 16 to 24 hours;

e) washing said filter for 20 minutes at room temperature in 1×SSC, 0.1% SDS; and f) washing said filter three times for 20 minutes each at 68° C. in 0.2×SSC, 0.1SDS; and g) autoradiographing said filter by exposing said filter for 24 to 48 hours to X-ray film at −70° C. with an intensifying screen.

6. An isolated fungus responsive promoter comprising a fungus responsive promoter element with a length of about 402 nucleotides, wherein said fungus-responsive promoter element hybridizes in a conventional manner with a DNA probe consisting of the nucleotide sequence of SEQ ID No. 1 from the nucleotide at position 295 to the nucleotide at position 567 and wherein said conventional hybridization comprises the following consecutive steps:

a) immobilizing plant genomic DNA fragments on a filter;

b) prehybridizing said filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS;

c) adding said hybridization probe consisting of the nucleotide sequence of SEQ ID No. 1 from the nucleotide at position 295 to the nucleotide at position 567 which has been radiolabeled;

d) incubating for 16 to 24 hours;

e) washing said filter for 20 minutes at room temperature in 1×SSC, 0.1% SDS; and f) washing said filter three times for 20 minutes each at 68° C. in 0.2×SSC, 0.1SDS; and g) autoradiographing said filter by exposing said filter for 24 to 48 hours to X-ray film at −70° C. with an intensifying screen.

7. An isolated fungus responsive promoter comprising a fungus responsive promoter element with a length of about 428 nucleotides, wherein said fungus-responsive promoter element hybridizes in a conventional manner with a DNA probe consisting of the nucleotide sequence of SEQ ID No. 1 from the nucleotide at position 295 to the nucleotide at position 567 and wherein said conventional hybridization comprises the following consecutive steps:

a) immobilizing plant genomic DNA fragments on a filter;

b) prehybridizing said filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS;

c) adding said hybridization probe consisting of the nucleotide sequence of SEQ ID No. 1 from the nucleotide at position 295 to the nucleotide at position 567 which has been radiolabeled;

d) incubating for 16 to 24 hours;

e) washing said filter for 20 minutes at room temperature in 1×SSC, 0.1% SDS; and f) washing said filter three times for 20 minutes each at 68° C. in 0.2×SSC, 0.1SDS; and g) autoradiographing said filter by exposing said filter for 24 to 48 hours to X-ray film at −70° C. with an intensifying screen.

8. An isolated fungus responsive promoter from potato comprising an about 428 bp Sau3A1/StyI DNA fragment, wherein said DNA fragment hybridizes in a conventional manner with a DNA probe consisting of the nucleotide sequence of SEQ ID No. 1 from the nucleotide at position 295 to the nucleotide at position 567 and wherein said conventional hybridization comprises the following consecutive steps:

a) immobilizing plant genomic DNA fragments on a filter;

b) prehybridizing said filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS;

c) adding said hybridization probe consisting of the nucleotide sequence of SEQ ID No. 1 from the nucleotide at position 295 to the nucleotide at position 567 which has been radiolabeled;

d) incubating for 16 to 24 hours;

e) washing said filter for 20 minutes at room temperature in 1×SSC, 0.1% SDS; and f) washing said filter three times for 20 minutes each at 68° C. in 0.2×SSC, 0.1SDS; and g) autoradiographing said filter by exposing said filter for 24 to 48 hours to X-ray film at −70° C. with an intensifying screen.

9. An isolated fungus responsive promoter from potato comprising a nucleotide sequence of about 273 nucleotides downstream of a Sau3A1 site, wherein said nucleotide sequence hybridizes in a conventional manner with a DNA probe consisting of the nucleotide sequence of SEQ ID No. 1 from the nucleotide at position 295 to the nucleotide at position 567 and wherein said conventional hybridization comprises the following consecutive steps:

a) immobilizing plant genomic DNA fragments on a filter;

b) prehybridizing said filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS;

c) adding said hybridization probe consisting of the nucleotide sequence of SEQ ID No. 1 from the nucleotide at position 295 to the nucleotide at position 567 which has been radiolabeled;

d) incubating for 16 to 24 hours;

e) washing said filter for 20 minutes at room temperature in 1×SSC, 0.1% SDS; and f) washing said filter three times for 20 minutes each at 68° C. in 0.2×SSC, 0.1SDS; and g) autoradiographing said filter by exposing said filter for 24 to 48 hours to X-ray film at −70° C. with an intensifying screen.

10. An isolated fungus responsive promoter from potato comprising a nucleotide sequence of about 402 nucleotides downstream of a Sau3A1 site, wherein said nucleotide sequence hybridizes in a conventional manner with a DNA probe consisting of the nucleotide sequence of SEQ ID No. 1 from the nucleotide at position 295 to the nucleotide at position 567 and wherein said conventional hybridization comprises the following consecutive steps:

a) immobilizing plant genomic DNA fragments on a filter;

b) prehybridizing said filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS;

c) adding said hybridization probe consisting of the nucleotide sequence of SEQ ID No. 1 from the nucleotide at position 295 to the nucleotide at position 567 which has been radiolabeled;

d) incubating for 16 to 24 hours;

e) washing said filter for 20 minutes at room temperature in 1×SSC, 0.1% SDS; and f) washing said filter three times for 20 minutes each at 68° C. in 0.2×SSC, 0.1SDS; and g) autoradiographing said filter by exposing said filter for 24 to 48 hours to X-ray film at −70° C. with an intensifying screen.

11. An isolated fungus responsive promoter from potato comprising a nucleotide sequence of about 428 nucleotides downstream of a Sau3A1 site, wherein said nucleotide sequence hybridizes in a conventional manner with a DNA probe consisting of the nucleotide sequence of SEQ ID No. 1 from the nucleotide at position 295 to the nucleotide at position 567 and wherein said conventional hybridization comprises the following consecutive steps:

a) immobilizing plant genomic DNA fragments on a filter;

b) prehybridizing said filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS;

c) adding said hybridization probe consisting of the nucleotide sequence of SEQ ID No. 1 from the nucleotide at position 295 to the nucleotide at position 567 which has been radiolabeled;

d) incubating for 16 to 24 hours;

e) washing said filter for 20 minutes at room temperature in 1×SSC, 0.1% SDS; and f) washing said filter three times for 20 minutes each at 68° C. in 0.2×SSC, 0.1SDS; and g) autoradiographing said filter by exposing said filter for 24 to 48 hours to X-ray film at −70° C. with an intensifying screen.

12. A chimeric gene comprising the isolated fungus responsive promoter of any one of claims 2 to 11 operably linked to a foreign DNA sequence.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 1972 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: potato cv. Datura (ix) FEATURE:
      (A) NAME/KEY: -
      (B) LOCATION: 1..6
      (D) OTHER INFORMATION: /note= "EcoRI site at position 1-6."

(ix) FEATURE:
      (A) NAME/KEY: -
      (B) LOCATION: 295..298
      (D) OTHER INFORMATION: /note= "Sau3AI site at position 295-298."

(ix) FEATURE:
      (A) NAME/KEY: -
      (B) LOCATION: 643
      (D) OTHER INFORMATION: /note= "5' end of putative TATA box at position 643."

(ix) FEATURE:
      (A) NAME/KEY: -
      (B) LOCATION: 751
      (D) OTHER INFORMATION: /note= "ATG translation initiation condon at position 751."

(ix) FEATURE:
      (A) NAME/KEY: -
      (B) LOCATION: 1809
      (D) OTHER INFORMATION: /note= "UGA stop condon at position 1809."

(xi) SEQUENCE DESCRIPTION: SEQ ID NO:1:

```
GAATTCAGGA AGAATTTTGT AGGTTCAACT AAATTATATA TATATATATA AAAAAATAAA        60

AATTATTAGA CGCTTCGACT ATTTACTTAC TTTAAAATTT GAATTTTCGT ACGAATAAAA       120

TTATTTGTCA GAGAAAAGTC TTTTAGCTAT TCACATGCTA GGAAGTTTCA CTTTTGGTGG       180

ATCAGTGATT GTATATTATT TAATATATAT CAATTTTCTC ATCAAACTGA AAATGAAAGA       240

TAAAATTAAT ATTAAAAACT CCATTCATTT TAATTTATTG TCATGTTTTG ACTTGATCCA       300

AAATCTAACA ATTTAAAAGG TTTTAAATTT TTGTGCTTTT TTTTAAATTA AAAATATGTC       360

AAATATATTA AAATATATTT TTTAAATTTT ATACTAAAAA ACATGTCACA TGAATATTTG       420

AAATTATAAA ATTATCAAAA ATAAAAAAAG AATATTTCTT TAACAAATTA AAATTGAAAA       480

TATGATAAAT AAATTAAACT ATTCTATCAT TGATTTTTCT AGCCACCAGA TTTGACCAAA       540
```

```
CAGTGGGTGA CATGAGCACA TAAGTCATCT TTATTGTATT TTATTACTCA CTCCAAAAAT      600

ATAGGGAATA TGTTTACTAC TTAATTTAGT CAAATATAAT TTTATATTAG AATAATTGAA      660

TAGTCAAACA AGAAACTTTA ATGCATCCTT ATTTTTTCCT CTATAAAAAA AAGACTAGAC      720

ACCAAGGGAG ACCAACCACA CATAATTAAG ATGGCAGAAG TGAAGTTGCT TGGTCTAAGG      780

TATAGTCCTT TTAGCCATAG AGTTGAATGG GCTCTAAAAA TTAAGGGAGT GAAATATGAA      840

TTTATAGAGG AAGATTTACA AAATAAGAGC CCTTTACTTC TTCAATCTAA TCCAATTCAC      900

AAGAAAATTC CAGTGTTAAT TCACAATGGC AAGTGCATTT GTGAGTCTAT GGTCATTCTT      960

GAATACATTG ATGAGGCATT TGAAGGCCCT TCCATTTTGC CTAAAGACCC TTATGATCGC     1020

GCTTTAGCAC GATTTTGGGC TAAATACGTC GAAGATAAGG TATATTGCTT TTAAGTTATT     1080

CCAATTGATT GAAAAGTTTG TTTTAGTTAC GTTATTACAT ATACTTTAGG TCTCATGCTT     1140

TTTAATAATC TTTTATAAAA TTCGACTAAG ACGAACTTCT CGTATAGTCA ACAATACTAA     1200

CATATTTGTC TAGTAGTTGG TTAGGAAATA AGTTATCCGA ATATTAAATT CTGGATAAGT     1260

AATGAATACC ATATTTGATA GTTGATTTGG AGATAAATTA TTCGTGTATA AAATTAATAT     1320

GATATTTGAT TTGCAATTTA GAAATACATA ACTATTTTAT ATGCATAGAT CCATTATAAC     1380

TAATTGATAT ATTATTAATA TCTGTATAAC TCTAACCAGC TATCGAAACG AGTCAACGAA     1440

CCTTATTAAG TTTTGTTTGT TGGGCAGGGG GCAGCAGTGT GGAAAAGTTT CTTTTCGAAA     1500

GGAGAGGAAC AAGAGAAAGC TAAAGAGGAA GCTTATGAGA TGTTGAAAAT TCTTGATAAT     1560

GAGTTCAAGG ACAAGAAGTG CTTTGTTGGT GACAAATTTG GATTTGCTGA TATTGTTGCA     1620

AATGGTGCAG CACTTTATTT GGGAATTCTT GAAGAAGTAT CTGGAATTGT TTTGGCAACA     1680

AGTGAAAAAT TTCCAAATTT TTGTGCTTGG AGAGATGAAT ATTGCACACA AAACGAGGAA     1740

TATTTTCCTT CAAGAGATGA ATTGCTTATC CGTTACCGAG CCTACATTCA GCCTGTTGAT     1800

GCTTCAAAAT GAGTATACCT CAAGTGAATT TCAAGATTTT GTGTGGCAAT AAAAATTGAG     1860

TTTTTGTAAA TTCAATTGAA ATATATTAAA GTTGCATGTT ATAAGATTTA TCTTTATTTC     1920

ACTAGTTAAT ATAAATTTTG GATTCACGTA TAAATAAAAG TATTGTTAAG AG             1972
```